United States Patent [19]

Klenk et al.

[11] 4,108,877

[45] Aug. 22, 1978

[54] PROCESS FOR THE PRODUCTION OF ACYL CYANIDES (A)

[75] Inventors: Herbert Klenk; Heribert Offermanns, both of Hanau; Werner Schwarze, Frankfurt, all of Germany

[73] Assignee: Deutsche Gold- und Silber-Scheideanstalt Vormals Roessler, Frankfurt, Germany

[21] Appl. No.: 802,944

[22] Filed: Jun. 2, 1977

[30] Foreign Application Priority Data

Feb. 25, 1977 [DE] Fed. Rep. of Germany ....... 2708183

[51] Int. Cl.² ............... C07D 307/36; C07C 57/00; C07C 63/06
[52] U.S. Cl. .................. 260/347.8; 260/332.3 R; 260/545 R
[58] Field of Search ......... 260/545 R, 347.8, 332.3 R, 260/332.3 P

[56] References Cited

U.S. PATENT DOCUMENTS

4,069,252   1/1978   Findeisen et al. .............. 260/545 R

OTHER PUBLICATIONS

Normant et al., Bull. Soc. Chim. France, 1972, pp. 2402–2403.

*Primary Examiner*—Gerald A. Schwartz
*Attorney, Agent, or Firm*—Cushman, Darby & Cushman

[57] ABSTRACT

There are prepared acyl cyanides of the formula

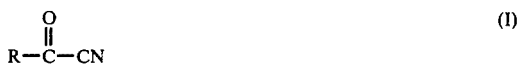

where R is a straight or branched chain alkyl group having 1 to 18 carbon atoms, preferably 1 to 10 carbon atoms, and which also can be substituted by one or more phenyl groups or halogen atoms, preferably chlorine, or R is preferably a cycloalkyl group having 3 to 8 carbon atoms, preferably cyclopropyl, which can have one or more 1 to 3 carbon atom alkyl or halogen, preferably chlorine, substituents wherein in all of the above set forth substitutions the halogen atoms and the phenyl groups are not on the carbon atom adjacent to the carbonyl group or R is a substituted phenyl group, a naphthyl group, a substituted naphthyl group or a five membered heterocyclic group, e.g., furyl, thienyl or alkyl substituted thienyl, wherein the substituents on the phenyl or naphthyl are halogen atoms, nitro groups or alkyl or alkoxy groups having 1 to 5 carbon atoms. The process comprises reacting an acyl halide of the formula

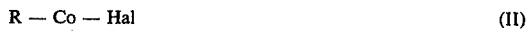

in which R is as defined above and Hal is a chlorine or bromine atom, with CuCN at a temperature of about 50° to 180° C in the presence of a carboxylic acid nitrile inert under the reaction conditions, there being employed about 1 to 10 parts by weight of the carboxylic acid nitrile and about 0.5 to 20 parts by weight of at least one organic solvent which is inert under the reaction conditions. Certain of the compounds are novel per se.

22 Claims, No Drawings

PROCESS FOR THE PRODUCTION OF ACYL CYANIDES (A)

BACKGROUND OF THE INVENTION

The invention concerns a process for the production of acyl cyanides by reaction of carboxylic acid halides with metal cyanides at elevated temperature. Acyl cyanides are important intermediate products for example for the production of α-ketocarboxylic acids.

It is known that acyl cyanides can be produced by reacting a metal cyanide with a carboxylic acid halide. However, the previously known processes have considerable disadvantages.

Thus, in the production of aliphatic acyl cyanides there must be employed acid bromides since the reactability of the acid chloride is not sufficient. For example, acetyl chloride does not react with CuCN even at the boiling temperature and likewise no reaction is obtained with KCN at a temperature between 65° and 130° C (C. D. Hurd, O. E. Edwards, J. R. Roach, J. Amer. Chem. Soc. 66 (1944), 2014). With pivaloyl chloride and CuCN to be sure it is possible to obtain a reaction but the reaction time of 20 hours is extremely long (N. Sperber, R. Frican, J. Amer. Chem. Soc. 72 (1950), 2793).

It is also known to react certain aliphatic carboxylic acid nitriles with CuCN in boiling acetonitrile but the yields are very small. Thus, starting from acetyl chloride there is isolated only 50% of acetyl cyanide and from pivaloyl chloride only 16% pivaloyl cyanide (Normant, Bull. Soc. Chim. France, 1972, pages 2402–2403). Somewhat higher yields of benzoyl, p-nitrobenzoyl cyanide and p-methoxybenzoyl cyanide are shown as well as valeroyl cyanide.

Aroyl cyanides are somewhat more easily produced from aroyl chlorides and metal cyanides, but the reaction conditions are still very disagreeable. For example, in the production of p-methoxybenzoyl cyanide from p-methoxybenzoyl chloride there is used mercury cyanide and a temperature range of 125° to 130° C (L. Rosenthal, Berichte deutsch Chem. Gesell. 44 (1911), 2465).

SUMMARY OF THE INVENTION

There has now been found a process for the production of acyl cyanides of the formula

(I)

where R is a straight or branched chain alkyl group having 1 to 18 carbon atoms, preferably 1 to 10 carbon atoms, and which also can be substituted by at least one phenyl group or halogen atom, preferably chorine, or R is preferably a cycloalkyl group having 3 to 8 carbon atoms, preferably cyclopropyl, which can have at least one alkyl substituent having 1 to 3 carbon atoms or halogen, preferably chlorine, with the proviso that in all of the above set forth substituents the halogen atoms and the phenyl groups are not on the carbon atom adjacent to the carbonyl group or R is a substituted phenyl group, a naphthyl group, a substituted naphthyl group or a five membered heterocyclic group, e.g., furyl, thienyl or alkyl substituted thienyl, wherein the substituents on the phenyl or naphthyl are halogen atoms, nitro groups, alkyl groups having 1 to 5 carbon atoms or alkoxy groups having 1 to 5 carbon atoms. The process comprises reacting an acyl halide of the formula $$R — CO — Hal \qquad (II)$$

in which R is as defined above and Hal is a chlorine or bromine atom with CuCN at a temperature of about 50° to 180° C in the presence of a mixture consisting of about 1 to 10 equivalents of a carboxylic acid nitrile inert under the reaction conditions, and about 0.5 to 20 parts by weight of at least one organic solvent which is inert under the reaction conditions.

It is completely surprising that the reaction succeeds with both aromatic, e.g., aroyl, as well as aliphatic, e.g., acyl halides and with both acid bromides and acid chlorides and in all cases leads to very good yields.

Illustrative acyl halides of formula (II) which can be used in the reaction are acetyl chloride, pivaloyl chloride, propionyl chloride, isobutyryl chloride, isovaleroyl chloride, stearoyl chloride, decanoyl chloride, hexanoyl chloride, isodecanoyl chloride, furoyl chloride, 4-chlorobutyryl chloride, 3-chloropropionyl chloride, 5-chlorovaleroyl chloride, 3,3-dichloropropionyl chloride, 3-phenylpropionyl chloride, 4-phenylbutyryl chloride, 3-bromopropionyl chloride, 2-methylbutyryl chloride, (cyclopropane carboxylic acid chloride), cyclohexane carboxylic acid chloride, 1-methylcyclohexane carboxylic acid chloride, 1-methyl-2,2-dichlorocyclopropane carboxylic acid chloride, 1,3-dimethyl-2,2-dichlorocyclopropane carboxylic acid, 1,3-dimethylcyclopropane carboxylic acid chloride, cyclopentane carboxylic acid chloride, cyclooctane carboxylic acid chloride, 1-naphthoyl chloride, 2-naphthoyl chloride, 2-methylbenzoyl chloride, 3-methylbenzoyl chloride, 4-methylbenzoyl chloride, 2,4-dimethylbenzoyl chloride, 2-methyl-4-chlorobenzoyl chloride, 2,4-dichlorobenzoyl chloride, 4-chlorobenzoyl chloride, 2-chlorobenzoyl chloride, 4-fluorobenzoyl chloride, 4-nitrobenzoyl chloride, 3-nitrobenzoyl chloride, 4-ethylbenzoyl chloride, 4-isopropylbenzoyl chloride, 4-amylbenzoyl chloride, 4-t-amylbenzoyl chloride, 2-methoxybenzoyl chloride, 4-methoxybenzoyl chloride, 2,4-dimethoxybenzoyl chloride, 3-ethoxybenzoyl chloride, 3,4-dimethoxybenzoyl chloride, 4-amyloxybenzoyl chloride, 2-bromobenzoyl chloride, 1-propylcyclopropane carboxylic acid chloride, 2-chloronaphthoyl chloride, 3-nitronaphthoyl chloride, 2-methylnaphthoyl chloride, 2-methoxynaphthoyl chloride, acetyl bromide, pivaloyl bromide, 4-chlorobenzoyl bromide, cyclopropane carboxylic acid bromide.

The acyl halides of formula II can be prepared by known method. E.g. 2,2-dichloro-1-methylcyclopropyl carbonic acid is reacted with the equivalent amount of thionyl chloride at about 18° C and the reaction product is distilled under reduced pressure.

Besides the simple procedure a substantial advantage of the process of the invention is that it is not limited to the production of special acyl cyanides, but it is virtually universally usable and it can be used to prepare previously unknown compounds, for example, (2,2-dichloro-1-methylcyclopropyl)-glyoxylnitrile and (2,2-dichloro-1,3-dimethylcyclopropyl)-glyoxylnitrile.

These latter compounds are useful to prepare the corresponding alpha keto carboxylic acids. They also are useful for insecticides.

The reaction takes place in the presence of at least one carboxylic acid nitrile which is inert under the reaction conditions. Well suited are nitriles of simple monocarboxylic acids such as propionitrile or benzonitrile. There can also be used for example butyronitrile, isobutyronitrile, valeronitrile, capronitrile, caprylonitrile, lauronitrile, o-toluonitrile, p-toluonitrile or m-toluonitrile. Preferred nitrile is acetonitrile. Although very large amounts of nitrile can be used it is advantageous to add only a slight overstoichiometric amount of carboxylic acid nitrile. Preferably there is used about 1.05 to 5.0 equivalents (moles) of carboxylic acid nitrile per mole of acid halide. Less preferably there can be used less nitrile, e.g., about 0.1 to 1.0 mole of nitrile per mole of acid halide.

The reaction takes place in the presence of CuCN. It is generally suitable to use overstoichiometric amounts of CuCN. It is advantageous to use 1.05 to 2 equivalents (moles) of CuCN per mole of acid halide.

As inert organic solvents there can be used, for example, hydrocarbons, e.g., aromatic hydrocarbons such as benzene, toluene or xylene as well as mesitylene, ethyl benzene, cumene, p-cymene, t-butyl benzene or 1,3,5-triethyl benzene or aliphatic hydrocarbons such as ligroin with a boiling range of about 90° to 140° C, pentane, hexane, heptane, octane or decane or cyclic hydrocarbons, such as decalin, cyclohexane and tetralin or halogenated hydrocarbons, particularly chlorinated aromatic or aliphatic hydrocarbons, such as chlorobenzene, dichlorobenzene, symmetrical tetrachloroethane, chloroform. dichloroethylene, carbon tetrachloride, trichloroethylene, methylene chloride, trimethylene bromide, dibromoethylene, ethylene dibromide. Also as the solvent there can be used for example ethers, e.g., dioxane, dibutyl ether, dioxolane, ethylene glycol diethyl ether, ethylene glycol dibutyl ether, ethylene glycol dimethyl ether or esters, e.g., alkyl esters, e.g., alkyl alkanoates, such as butyl acetate, propyl acetate, amyl acetate, isobutyl acetate, octyl acetate, ethyl propionate, methyl butyrate, ethyl butyrate or methyl valerate. Mixtures of such solvents can be used.

In selecting the inert organic solvent to use both as to type and amount the thought is to make it easy to separate it from the acyl cyanide formed.

The reaction temperature can be varied within wide limits and depends on the type of solvent and the reactants. Generally, there is used a temperature of about 50° to about 180° C, particularly from 70° to 130° C. Although the pressure can be selected substantially at random it is advantageous not to deviate substantially from normal pressure, i.e., atmospheric pressure.

Unless otherwise indicated, all parts and percentages are by weight.

The materials employed can comprise, consist essentially of or consist of those set forth.

DESCRIPTION OF THE PREFERRED EMBODIMENTS

EXAMPLE 1

There were mixed in a reaction vessel provided with a reflux condenser 154.5 grams (1.0 mole) of 4-methylbenzoyl chloride with 117 grams (1.3 moles) of copper (I) cyanide, 150 ml of toluene and 61.5 grams (1.5 moles) of acetonitrile. The mixture was heated to 110° C with stirring, held for 3 hours at this temperature and then cooled to 20° C. The salt separated thereby was filtered off and washed twice, each time with 50 ml of toluene. The filtrate was fractionally distilled at reduced pressure. There were recovered 137 grams of pure 4-methylbenzoyl cyanide, corresponding to a yield of 95% based on the acid chloride employed. The 4-methyl-benzoyl cyanide had a boiling point of 100° to 103° C at 20 mbar.

EXAMPLE 2

The procedure was the same as that described in Example 1 but instead of toluene there were used 250 ml of dichloroethane and the mixture was heated only to 90° C. There were isolated 125 grams of 4-methylbenzoyl cyanide, corresponding to a yield of 87% based on the acid chloride employed. The 4-methylbenzoyl cyanide had a boiling point of 107° to 110° C at 28 mbar.

EXAMPLE 3

Using the method described in Example 1, there were produced the compounds entered in the following table:

R—CO—CN

| Compound Number | R | Yield (%) | Boiling Point C | / | mbar |
|---|---|---|---|---|---|
| 1 | 2-methylphenyl | 90 | 108–110 | / | 20 |
| 2 | 4-chlorophenyl | 87 | 114–116 | / | 17 |
| 3 | 2-chlorophenyl | 87 | 120–123 | / | 17 |
| 4 | 4-fluorophenyl | 85 | 85–88 | / | 20 |
| 5 | 4-nitrophenyl | 75 | 162–163 | / | 17 |
| 6 | 4-methoxyphenyl | 91 | 157–158 | / | 16 |
| 7 | 2-furyl | 83 | 74–77 | / | 15 |
| 8 | 1-methylnaphthyl | 90 | 179–182 | / | 20 |
| 9 | 2-naphthyl | 90 | 150 | / | 7 |
| 10 | 1-methylcyclohexyl | 92 | 79–81 | / | 17 |

-continued

| Compound Number | R | Yield (%) | Boiling Point C | / | mbar |
|---|---|---|---|---|---|
| 11 | Cl₂C(H)-C(CH₃)- (cyclopropyl with Cl, Cl, H₂, CH₃) | 84 | 81–82 | / | 14 |
| 12 | C₆H₅-CH₂-CH₂- | 80 | 117–119 | / | 15 |
| 13 | Cl-CH₂-CH₂-CH₂- | 76 | 88 | / | 25 |
| 14 | cyclopropyl with Cl, Cl, H, CH₃, CH₃ | 70 | 85–86 | / | 10 |

EXAMPLE 4

There were mixed in a reaction vessel provided with a reflux condenser 157.0 grams (2.0 moles) of acetyl chloride with 270 grams (3 moles) of copper (I) cyanide, 400 ml of 1,2,3,4-tetrahydronaphthalene and 164 grams (4 moles) of acetonitrile. The mixture was heated to boiling with stirring and held for 4 hours at reflux. Then it was cooled, the salt filtered off and washed twice, each time with 50 ml of tetrahydronaphthalene. The filtrate was fractionally distilled. The first fraction having a head temperature of 110° C was removed. The weight of this fraction was 291 grams and contained according to gas chromatogram of 39.5% acetyl cyanide. This means a yield of 84% of acetyl cyanide based on the acetyl chloride employed.

EXAMPLE 5

The procedure was the same as in Example 4 except that instead of acetyl chloride there were used 241 grams (2.0 moles) of pivaloyl chloride. The fractional distillation resulted in 201 grams of pure pivaloyl cyanide, corresponding to a yield of 92% based on the pivaloyl chloride employed. The pivaloyl cyanide had a boiling point of 117° to 122° C at normal pressure.

EXAMPLE 6

The following compounds were produced by the process described in Example 5:

| Compound Number | R | Yield (%) | Boiling Point C | / | mbar |
|---|---|---|---|---|---|
| 1 | CH₃-CH₂- | 75 | 106–110 | / | 1015 |
| 2 | (CH₃)₂CH- | 80 | 61–62 | / | 133 |
| 3 | (CH₃)₂CH-CH₂- | 80 | 71–74 | / | 120 |
| 4 | CH₃-CH₂-C(CH₃)(H)- | 81 | 68–70 | / | 135 |

-continued

| Compound Number | R | Yield (%) | Boiling Point C | / | mbar |
|---|---|---|---|---|---|
| 5 | cyclopropyl (H, H, H, H) | 85 | 92–93 | / | 160 |

What is claimed is:

1. A process for the production of an acyl cyanide of the formula $$\underset{R-C-CN}{\overset{O}{\|}} \quad (I)$$

where R is alkyl having 1 to 18 carbon atoms, alkyl of 1 to 18 carbon atoms substituted by phenyl or halogen, cycloalkyl having 3 to 8 carbon atoms in alkyl group, cycloalkyl having 3 to 8 carbon atoms substituted by 1 to 3 carbon atoms alkyl or halogen with the proviso that any phenyl or halogen substituent on the alkyl or any halogen substituent on the cycloalkyl is not on the carbon atom adjacent to the carbonyl group or R is naphthyl, five membered heterocyclic group, substituted naphthyl or substituted phenyl wherein the substituent on the naphthyl or phenyl is halogen, nitro, alkyl of 1 to 5 carbon atoms or alkoxy of 1 to 5 carbon atoms comprising reacting at a temperature of about 50° to 180° C an acyl halide on the formula $$R - CO - Hal \quad (II)$$

where Hal is chlorine or bromine with CuCN in the presence of a mixture consisting of 1 to 10 equivalents of a carboxylic acid nitrile which is inert under the reaction conditions and about 0.5 to 20 parts by weight of an organic solvent which is inert under the reaction conditions, said solvent being a hydrocarbon, halohydrocarbon, ether or ester.

2. The process according to claim 1 wherein any halogen substituent on R is chlorine.

3. The process of claim 1 wherein Hal is chlorine.

4. The process of claim 1 where when R is heterocyclic the heterocyclic group is furyl.

5. The process of claim 1 wherein R is alkyl, cycloalkyl, substituted alkyl or substituted cycloalkyl.

6. The process of claim 5 wherein R is alkyl, cycloalkyl, chloroalkyl, alkyl substituted cycloalkyl, chloro substituted cycloalkyl or both chloro and alkyl substituted cycloalkyl, the cycloalkyl group having 3 to 6 carbon atoms.

7. The process of claim 6 wherein R is alkyl of 1 to 10 carbon atoms.

8. The process of claim 6 wherein R is cycloalkyl or cycloalkyl having 1 to 4 substituents, the substituents being methyl or chloro with not over two of the substituents being either methyl or chloro.

9. The process of claim 6 wherein R is cyclopropyl or substituted cyclopropyl.

10. The process of claim 5 wherein R is phenyl substituted alkyl, the alkyl having 1 to 10 carbon atoms.

11. The process of claim 1 wherein R is furyl.

12. The process of claim 1 wherein R is naphthyl, substituted naphthyl or substituted phenyl.

13. The process of claim 12 where R is naphthyl.

14. The process of claim 12 where R is substituted naphthyl.

15. The process of claim 12 where R is substituted phenyl.

16. The process of claim 1 wherein the inert organic solvent is a hydrocarbon or halohydrocarbon.

17. The process of claim 16 wherein the solvent is an aromatic hydrocarbon or a cycloaliphatic hydrocarbon.

18. The process of claim 1 wherein the nitrile is a lower alkyl nitrile or benzonitrile.

19. The process of claim 18 wherein the nitrile is acetonitrile.

20. The process of claim 1 wherein there is used 1.05 to 2 equivalents of CuCN per mole of (II) and Hal is chlorine.

21. The process of claim 20 wherein there are used 1.05 to 5.0 equivalents of nitrile per mole of acid chloride.

22. The process of claim 21 wherein the temperature is 70° to 130° C.

* * * * *